US012788514B2

(12) United States Patent
Simi et al.

(10) Patent No.: US 12,788,514 B2
(45) Date of Patent: Nov. 10, 2026

(54) MASTER WORKSTATION FOR ROBOTIC SURGERY, STERILE OPERATORY FIELD, SURGICAL ROBOTIC SYSTEM AND METHOD

(71) Applicant: MEDICAL MICROINSTRUMENTS, INC., Pisa (IT)

(72) Inventors: Massimiliano Simi, Pisa (IT); Federico Montagnani, Pisa (IT)

(73) Assignee: Medical Microinstruments, Inc., Wilmington, DE (US)

( * ) Notice: Subject to any disclaimer, the term of this patent is extended or adjusted under 35 U.S.C. 154(b) by 670 days.

(21) Appl. No.: 17/760,397

(22) PCT Filed: Feb. 10, 2021

(86) PCT No.: PCT/IB2021/051074
§ 371 (c)(1),
(2) Date: Aug. 9, 2022

(87) PCT Pub. No.: WO2021/161185
PCT Pub. Date: Aug. 19, 2021

(65) Prior Publication Data

US 2023/0075098 A1 Mar. 9, 2023

(30) Foreign Application Priority Data

Feb. 10, 2020 (IT) ........................ 102020000002554

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/74* (2016.02); *A61B 46/10* (2016.02); *A61B 50/13* (2016.02);
(Continued)

(58) Field of Classification Search
CPC ...... A61B 2034/2051; A61B 2034/742; A61B 2090/571; A61B 34/37; A61B 34/74;
(Continued)

(56) References Cited

U.S. PATENT DOCUMENTS

2005/0194507 A1 9/2005 White
2009/0301927 A1 12/2009 Fvlbrook
(Continued)

FOREIGN PATENT DOCUMENTS

EP 2845556 A1 3/2015
EP 2467082 B1 4/2016
(Continued)

OTHER PUBLICATIONS

International Search Report and Written Opinion for International Patent Application No. PCT/IB2021/051074, mailed May 7, 2021, 10 pp.
(Continued)

*Primary Examiner* — Scott Luan
(74) *Attorney, Agent, or Firm* — Armstrong Teasdale LLP

(57) ABSTRACT

A master workstation for a surgical robotic system suitable for being located within a sterile operatory field includes an ungrounded master input handle suitable for being hand held by a surgeon during surgery for controlling a slave robotic assembly of the surgical robotic system; a console; a sterile drape draping at least a portion of the console; and at least one sterile holder, wherein the at least one sterile holder
(Continued)

includes at least one cavity and at least one resting element within the cavity suitable for the master input handle to rest thereon when the master input handle is not hand held.

20 Claims, 8 Drawing Sheets

(51) Int. Cl.

| | |
|---|---|
| ***A61B 46/10*** | (2016.01) |
| ***A61B 50/13*** | (2016.01) |
| ***A61B 90/50*** | (2016.01) |
| ***A61B 90/60*** | (2016.01) |
| *A61B 90/57* | (2016.01) |

(52) U.S. Cl.
CPC .............. *A61B 90/50* (2016.02); *A61B 90/60* (2016.02); *A61B 2034/742* (2016.02); *A61B 2090/571* (2016.02)

(58) Field of Classification Search
CPC ......... A61B 46/10; A61B 50/13; A61B 90/50; A61B 90/57; A61B 90/60
See application file for complete search history.

(56) References Cited

U.S. PATENT DOCUMENTS

| | | | | |
|---|---|---|---|---|
| 2014/0018960 | A1 | 1/2014 | Itkowitz | |
| 2015/0101616 | A1 | 4/2015 | Wiley et al. | |
| 2021/0205039 | A1 * | 7/2021 | Simi ...................... | A61B 34/20 |

FOREIGN PATENT DOCUMENTS

| | | | |
|---|---|---|---|
| WO | 2014151621 | A1 | 9/2014 |
| WO | 2017064301 | A1 | 4/2017 |
| WO | 2018189729 | A1 | 10/2018 |
| WO | 2019099854 | A1 | 5/2019 |
| WO | 2019220409 | A1 | 11/2019 |

OTHER PUBLICATIONS

Examiner's Report in corresponding CA patent application No. 3,116,586, mailed Mar. 10, 2026, 7 pages.
Examiner's Report in corresponding CA patent application No. 3,116,586, mailed Oct. 1, 2024, 6 pages.

* cited by examiner

MASTER WORKSTATION FOR ROBOTIC SURGERY, STERILE OPERATORY FIELD, SURGICAL ROBOTIC SYSTEM AND METHOD

CROSS-REFERENCE TO RELATED APPLICATIONS

This application is a National Stage Application of International Patent Application No. PCT/IB2021/051074, having an International Filing Date of Feb. 10, 2021, which claims priority to Italian Application No. 102020000002554, filed Feb. 10, 2020, each of which is hereby incorporated by reference in its entirety.

FIELD OF THE INVENTION

It is an object of the present invention a master workstation for robotic surgery.

The master workstation according to the present invention is particularly suitable for being located within a sterile operatory field.

The present invention also relates to an operatory field and to a surgical robotic system comprising at least said master workstation.

Moreover, the present invention also relates to method for performing surgery.

BACKGROUND ART

Broadly in the medical field, sterile holsters have been provided for dropping medical suction tubes, as shown for example in document US-2005-0194507, as well as organizers have been provided for expendable supplies for medical patients as shown in document US-2009-0301927.

Robotic surgery apparatuses are used in robotic-aided surgery and generally comprise a surgeon master console for receiving a manual command from the surgeon, a robotic slave central tower (or robotic cart) and a plurality of robotic slave arms carrying one or more surgical instruments (end-effectors) extending from the slave central tower and controlled by means of said surgeon master console. Said one or more slave surgical instruments are distally attached to the robotic slave arms, in order to perform surgical procedures to a patient who lies within a sterile operatory field. Surgical drape draping non-disposable parts of the robotic apparatus is typically provided to avoid contamination of the sterile operatory filed that may be caused by the robotic surgery apparatus. Straps and strings may be provided on the outer surface of the surgical drape for the purpose of tying the drape around the robot reducing the volume of the drape so that it results substantially tight fit.

For example, documents WO-2017-064301 and WO-2018-189729 in the name of the same Applicant disclose solutions of robotic surgery system, suitable for miniaturize the surgical instrument resulting suitable, inter alia, for robot-aided microsurgery. Traditional (non-robotic) microsurgery requires the surgeon to operate together with an operating microscope, typically an optical microscope, able to magnify the surgery field and therefore robotic surgery apparatuses for microsurgery are suitably equipped with an operating microscope.

Microsurgery procedures are carried out in several phases of the reconstruction of biological tissues, such as for example in the execution of blood vessel anastomosis, comprising small diameter vessels and nerves, as well as in the reconstruction of anatomic parts after the occurrence of traumatic lesions, in re-vascularization of tissues, reattachment of limbs, in transplantation and replantation procedures. In the field of microsurgery, robotic apparatuses allow a high degree of miniaturization of the surgical instrument when compared to traditional microsurgery and allows at the same time to reduce the transmission of tremor to the slave surgical instrument of the robotic surgery system.

Robotic surgery apparatuses are also suitable for robot-aided laparoscopic surgery, where the surgical instruments and at least one camera are individually inserted inside the patient's body by means of a set of percutaneous trocars, and wherein a visualization screen visualizes the laparoscopic images of the inner patient's body acquired from the camera. Thanks to the robotic aid, it is reduced the fulcrum effect during surgery due to the lever arm formed across the length of each percutaneous rigid trocar during manipulation of traditional (non-robotic) laparoscopic surgical instruments. Moreover, thanks to the robotic aid, the laparoscopic surgeon is provided with an improved comfort during surgery due to the ergonomic features of the surgeon master console.

Remote surgeon master consoles have been provided for, as shown for example in documents US-2014-0018960 and EP-2845556. Generally, such remote surgeon master consoles comprise a visualization device, a surgeon seat and/or a surgeon forearm resting elements, and master input appendices hinged to the body of the master console to receive a manual command from the surgeon for controlling the slave surgical instrument. Thereby, the comfort of the laparoscopic surgeon is even enhanced in that he/she is not required to even attend the sterile field of the operatory room and can perform surgery from a non-sterile remote location.

However, to have a large physical distance between the team in the sterile operatory field and the surgeon handling the master input appendices at the remote master console may create communication problems during surgery among the team and in particular with the surgeon.

It is therefore felt the need for the surgeon to attend the sterile operatory filed, even in presence of a robotic surgery system.

Moreover, in some applications of the robotic-aided microsurgery it is desirable the presence of the surgeon within the sterile operatory field during the robotic-aided surgery. Thereby, during a single intervention, the microsurgeon can switch from robotic-aided microsurgery to traditional (non-robotic) microsurgery grabbing in hand traditional microsurgery tools, such as tweezers, and/or back to the surgeon master console. Document WO-2014-151621 discloses a system for alternating hand surgery and robotic surgery using a mechanically ungrounded master controller that is designed for being hand held by the surgeon.

Wearable and mechanically ungrounded master controllers are also known for example from documents WO-2019-099854 and EP-2467082, and typically comprise a pair of rings to fit the surgeon fingers integrally associated to a grip command interface of the ungrounded master controller.

Document WO-2019-220409 of the same Applicant discloses a sterile console for robotic surgery comprising a surgical chair comprising a pair of cups attached to the chair armrests for dropping the ungrounded master input tool.

Therefore, it is felt the need of a solution that allow the surgeon to effectively alternate robot-aided surgery and traditional hand surgery.

At the same time, it is felt the need to simplify the switching from robot-aided surgery to traditional surgery in a single intervention, and vice-versa.

Solution

It is a scope of the present invention to overcome the drawbacks mentioned with reference to the known art.

These and other scopes are achieved by a master workstation according to claim 1.

Some preferred embodiments are the subject of dependent claims.

According to an aspect of the present invention, a master workstation for a surgical robotic system comprises at least one ungrounded master input handle, suitable for being hand-held by a surgeon during surgery for controlling a slave robotic assembly of said surgical robotic system; and a console; and a sterile drape draping at least a portion of said console, and at least one sterile holder.

According to an aspect of the present invention, said at least one sterile holder delimits at least one cavity and comprises at least one resting element within said cavity suitable for the master input handle to rest thereon when said master input handle is not hand held and an opening to access said cavity.

The master workstation may comprise two sterile holders and two ungrounded master input handles, wherein each sterile holder is suitable to individually house one of said two ungrounded master input handles. The two sterile holders may be attached to the same outer surface of the surgical drape in two spaced apart desired locations.

Said at least one sterile holder and said surgical drape may be in single piece.

Said at least one sterile holder may comprise a positioning element to position the cavity of the at least one sterile holder at a desired location with respect to the outer surface of the surgical drape, the desired location may be near the console and within the sterile operatory field.

Said positioning element of the at least one sterile holder may comprise an adhesive layer, such as an adhesive strip, for attaching the at least one sterile holder to the outer surface of the surgical drape.

Said outer surface of the surgical drape may comprise an adhesive layer, such as an adhesive strip to attach the at least one sterile holder to the outer surface of the sterile drape. In such a case, the at least one sterile holder may comprise a mark and/or a sign acting as positioning element.

Said positioning element of the at least one sterile holder may comprise a positioning clip and said positioning body may comprise a convex body, so that the positioning clip elastically engages the convex body through and preferably also across the sterile drape, while preserving the sterility of the operatory field.

Thanks to the proposed solutions, a console, such as a surgical chair, when draped by a sterile barrier assembly exposes a cavity for the purpose of providing a resting element for a master input handle to rest thereon, for example during hand surgery.

The proposed solutions are particularly suitable for, although not exclusively limited to, robotic-aided microsurgery. Furthermore, the proposed solutions are particularly suitable for, although not exclusively limited to, microsurgical procedures that contemplates the alternation of hand microsurgery and robot-aided microsurgery.

FIGURES

Further features and advantages of the master workstation, of the system, of the sterile operatory field and of the method according to the invention will become apparent from the following description of its preferred examples of embodiment, given by way of indicative and non-limiting example, with reference to the accompanying figures wherein.

Figure 6A:
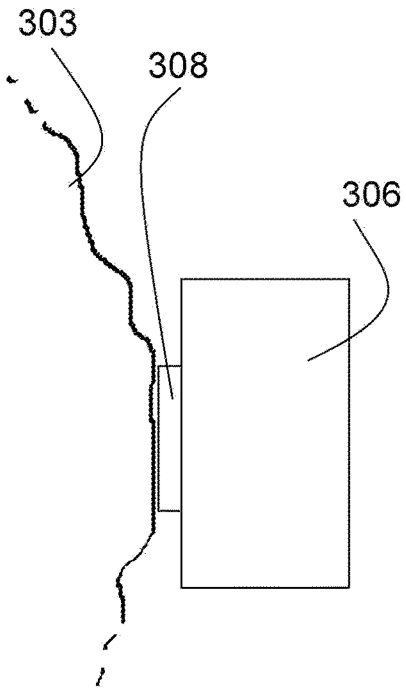
Figure 7:
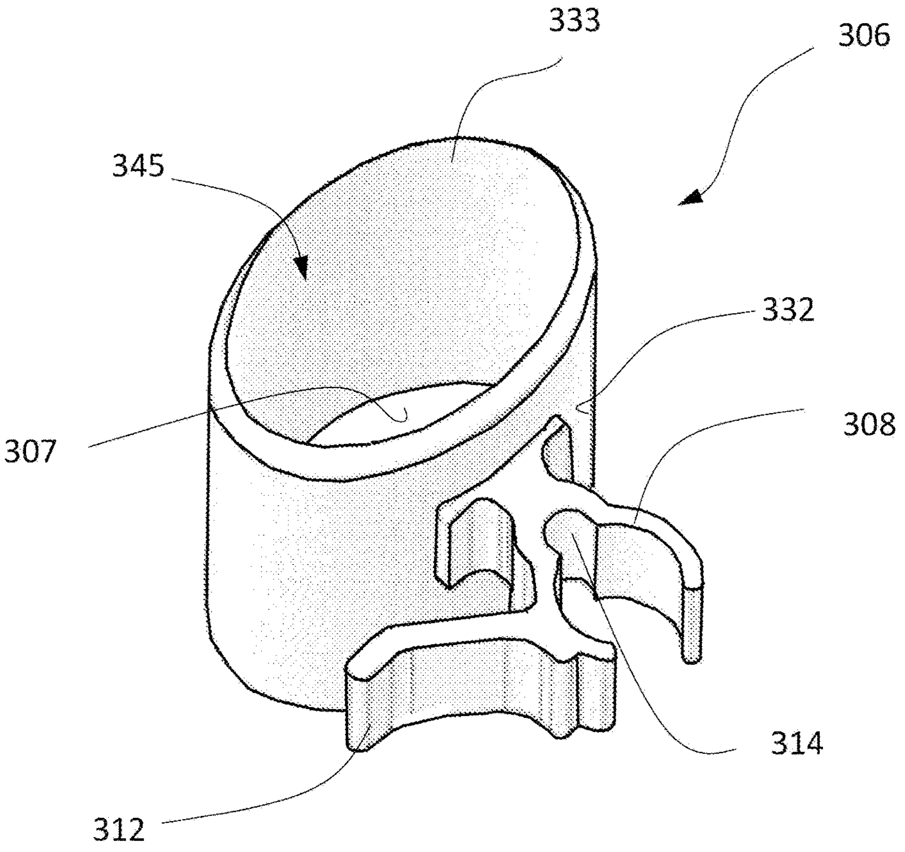
Figure 8:
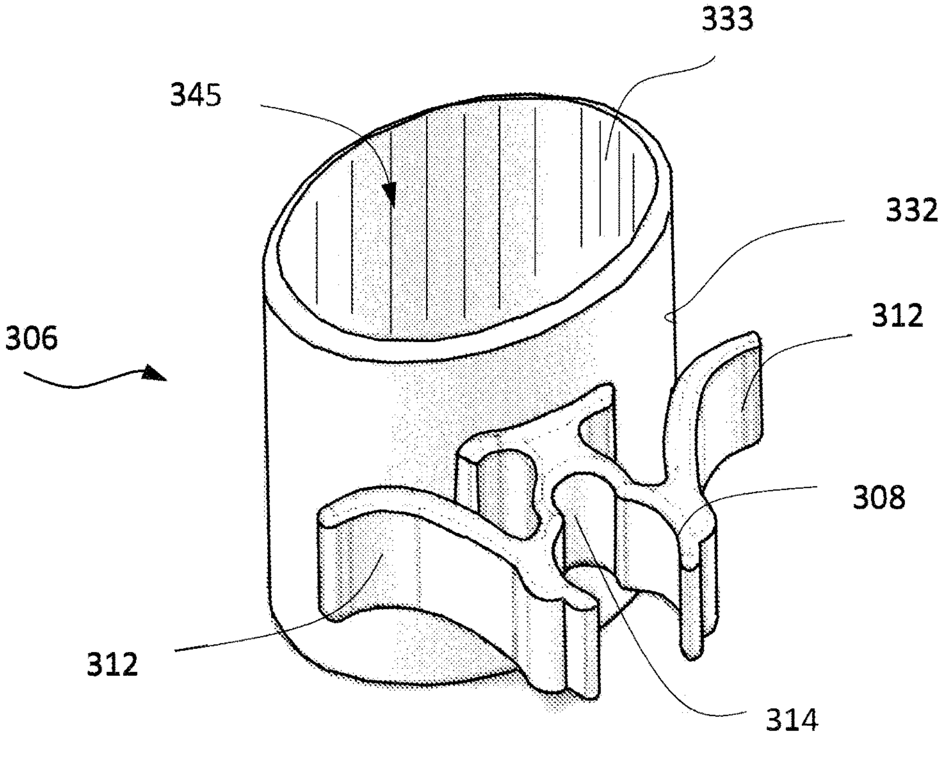
Figure 9:
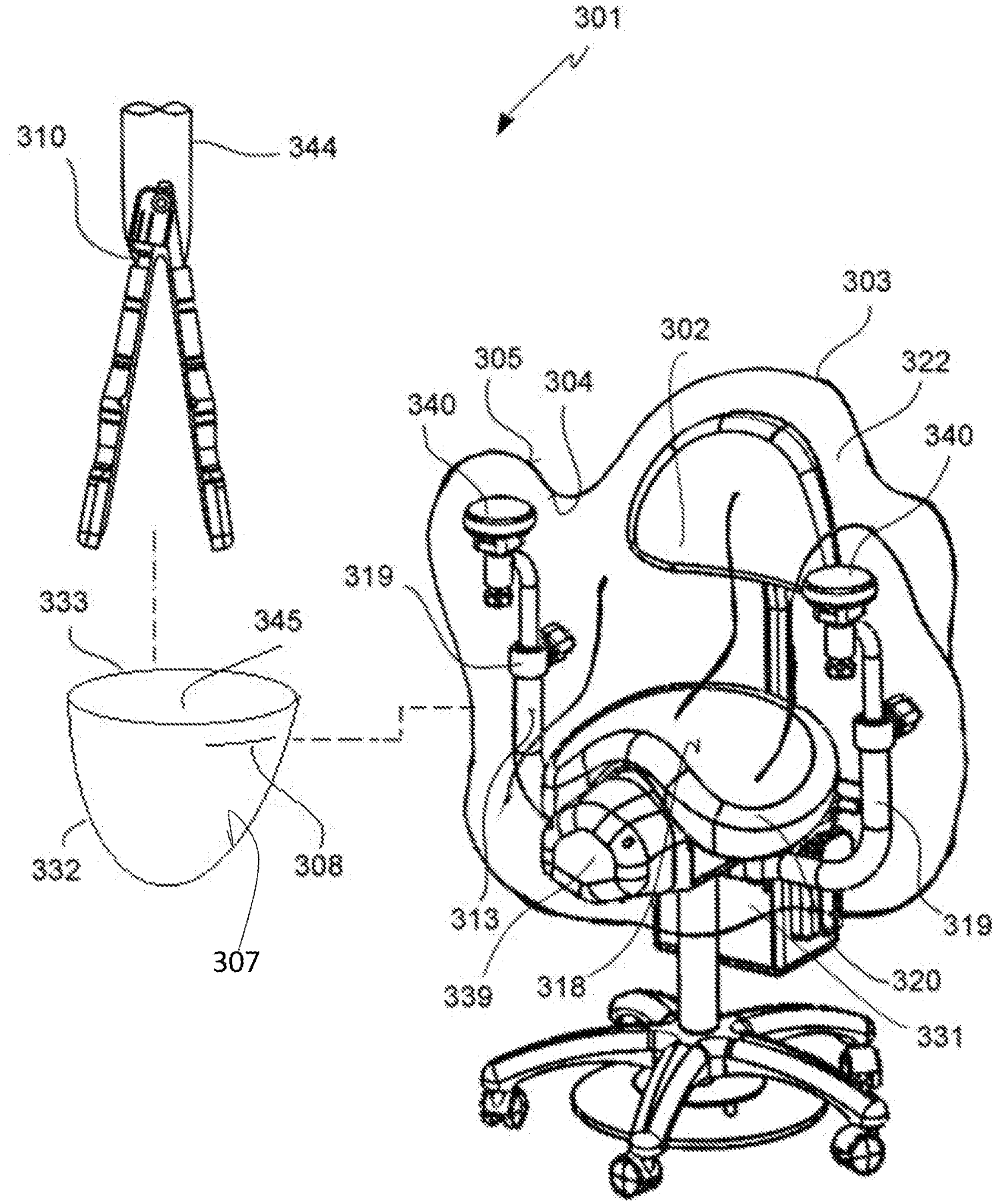
Figure 10:
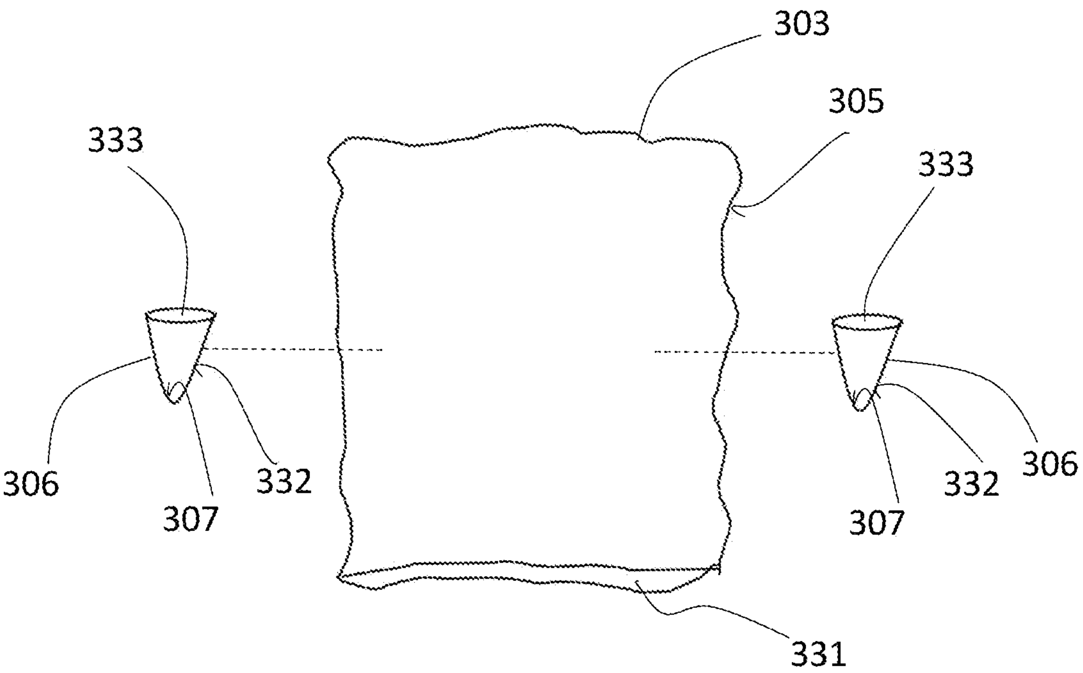
Figure 11:
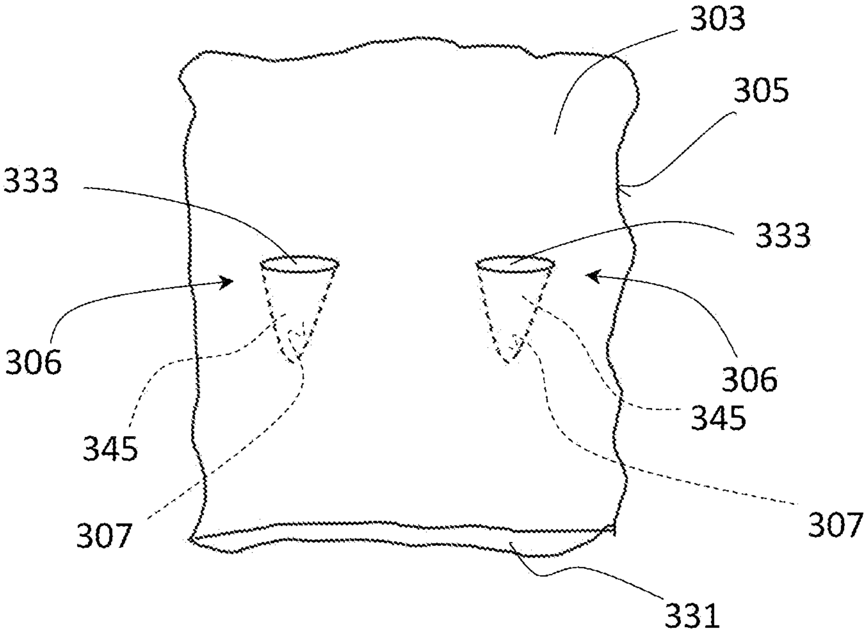
Figure 12:
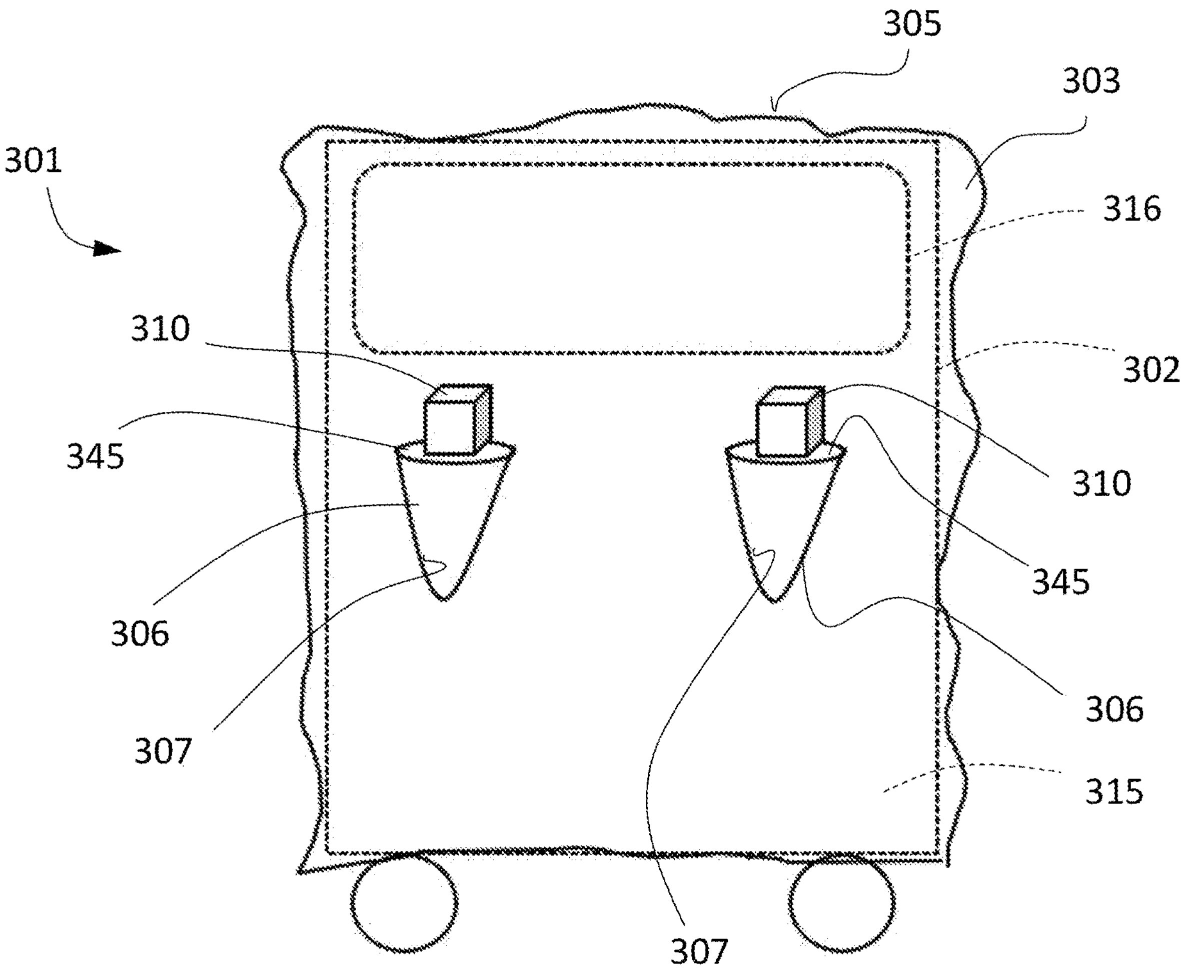

FIG. 6-A is an elevation side view diagrammatically showing a sterile holder and a sterile drape, according to an embodiment;

FIG. 6-B is an axonometric view showing the sterile holder integral with the sterile drape, according to an embodiment, from the inner side of the sterile drape;

FIG. 7 in an axonometric view showing a sterile holder, according to an embodiment;

FIG. 8 in an axonometric view showing a sterile holder, according to an embodiment;

FIG. 9 shows diagrammatically in axonometric view a master workstation comprising a draped console, a sterile holder and a draped master input handle, according to an embodiment;

FIG. 10 shows diagrammatically a pair of sterile holders associated to the outer surface of a surgical drape, according to an embodiment;

FIG. 11 shows diagrammatically a pair of sterile holders associated to the outer surface of a surgical drape, according to an embodiment;

FIG. 12 shows diagrammatically a master workstation comprising a draped console, a pair of sterile holders and a draped master input handle, according to an embodiment.

DETAILED DESCRIPTION OF SOME EMBODIMENTS

According to a general embodiment, it is provided a master workstation 301 for a surgical robotic system 300. The master workstation 301 is suitable for being located within a sterile operatory field 311.

The master workstation 301 comprises at least one mechanically ungrounded master input handle 310, suitable for being hand-held by a surgeon during surgery for controlling a slave robotic assembly 330 of said surgical robotic system 300.

As used herein, a "mechanically ungrounded master input handle 310" refers to a master controller that is unconstrained with respect to possible position and orientation motion in a large working environment e.g., an operating field or room and is kinematically separated from the ground, e.g., not mechanically supported by a console, any supports, or other object attached to the ground. In some implementations, a mechanically ungrounded master input handle 310 may be in tethered or untethered connection with one or more associated components such as control processors, data sources, sensors, power supplies, etc. For example, the master input handle 310 may be tethered, e.g., connected physically to these components via a cable or wire, or untethered, e.g., not physically connected to such components and in communication with the components via wireless communication signals. According to an embodiment, the master input handle 310 is mechanically unconstrained from said console 302. Moreover, the term "handle" means an ungrounded master input tool designed to be held in the surgeon's hand when in operative conditions. For example, said master input handle 310 may comprise a manipulandum portion suitable for being grasped by a surgeon's hand when in operative conditions. For example, said master input handle 310 may comprise a ring or an annular band or a bracelet to be worn by the surgeon's hand or finger or wrist.

The master workstation 301 further comprises a console 302 and a sterile drape 303 draping or covering at least a portion of said console 302. Said surgical drape 303 preferably has body having an inner surface 304, or non-sterile surface, and an outer surface 305, or sterile surface opposite to said inner non-sterile surface 304. Thereby, the inner surface 304 of the surgical drape 305 is designed to face the console 302 and the outer surface 305 of the surgical drape 303 is designed to face the sterile operatory field 311. According to a preferred embodiment, said surgical drape 303 forms a drape cavity 322 for enclosing a portion of said console 302 with the purpose of preserve sterility of the sterile operatory field 311. Thereby, the inner surface 304 faces the cavity 322, and the drape cavity 322 may be tight sealed or open forming an opening 331 to access the cavity 322 that leads to said outer surface 305 of the surgical drape 303. For example, the margin of said opening 331 or other parts of the drape 303 may fit the body of the console 302 by cooperating with adhesive strips, elastic strips, magnetic attraction or any suitable means. For example, the body of the surgical drape 303 is made of flexible sheet, such as polyethylene, and/or polyurethane, and/or polyester, and/or any suitable drape material, such as paper, and/or woven fabric, and/or non-woven fabric, and/or any combination of the above.

The console 302 may comprise at least one positioning body 309, for example a positioning body 309, and the sterile drape 303 drapes or covers at least a portion of said positioning body 309 of the console 302. As used herein, the term "convex body" does not necessarily exclude that the positioning body 309 may present a concave surface, but it must comprise also a convex portion or convex surface. For example, the term "convex body" also encompasses an upright of the console 302 having a substantially cylindrical outer surface, which is a convex body, comprising localized concave surfaces or portion or longitudinal grooves that defines a recess that in turn define a concave surface.

Said master workstation 301 comprises at least one sterile holder 306 comprising at least one cavity 345. Thereby the at least one sterile holder 306 acts a sterile basket and/or as a sterile pouch for dropping said at least one ungrounded master input handle 310.

Said at least one sterile holder 306 preferably comprises at least one opening 333 to access said cavity 345.

The opening 333 may open at the outer surface 305 of the surgical drape 303.

According to an embodiment, the at least one sterile holder 306 is made of plastic, preferably hard plastic material, and the cavity is for example molded or thermoformed. According to an embodiment, the holder 306 is made of sterilizable metallic material.

According to an embodiment, the at least one sterile holder 306 is made of plastic, preferably loose plastic material. According to an embodiment, the at least one sterile holder 306 is made of the same material of the surgical drape 303.

According to an embodiment, the at least one sterile holder 306 is in single piece with the outer surface 305 of the surgical drape 303, as shown for example in FIG. 11. For example, the at least one sterile holder 306 forms at least one pouch, which opens on the outer surface 305 of the sterile drape 303.

According to an embodiment, the at least one sterile holder 306 is disposable.

Advantageously, the at least one sterile holder 306 comprises at least one resting element 307 within said cavity 345. The at least one resting element 307 may be formed by the inner surface of the at least one sterile holder 306. The provision of said at least one resting element 307, for example at least one resting surface 307, within said cavity 345 of the at least one sterile holder 306 allows the master input handle 310 to rest thereon when said master input handle 310 is not hand-held, for example when is temporary not hand-held by a surgeon during surgery. Thereby, the at least one resting element 307 supports the master input handle 310 at least partially within the cavity 345 of the at least one sterile holder 306.

According to an embodiment, the at least one sterile holder 306 comprises at least one positioning element 308 to position the at least one sterile holder 306 at a desired location near the console 302 and preferably within the sterile operatory field 311.

According to an embodiment, said positioning element 308 of the at least one sterile holder 306 is engaged with at least one positioning body 309 of the console 302 through said sterile drape 303, while preserving the integrity of the sterile barrier formed at least partially by the sterile drape 303.

According to an embodiment, the sterile barrier is formed by the sterile drape 303 and by a portion of the outer wall 332 of the holder 306. The sterile drape 303 may be attached to the holder 306 and may comprise a through passage 348 for allowing the positioning element 308 to pass there through. The boundary 350 of the through passage 348 may be glued or welded or otherwise secured to the outer wall 332 of the sterile holder 306, as shown for example in FIG. 6B. Thereby, a portion of the outer wall 332 of the holder 306 acts as sterile barrier together with the sterile drape 303.

According to a preferred embodiment, the at least one sterile holder 306 comprises at least one positioning clip acting as positioning element 308 engaged with said at least one positioning body 309 through said sterile drape 303, while preserving the integrity of the sterile barrier, which is formed at least partially by the sterile drape 303. Thereby, said positioning clip 308 covers a portion of the outer surface 305 of the sterile drape 303, which thereby results put in between the positioning clip of the at least one sterile holder 306 and the positioning body 309 of the console 302, locally preserving the sterile operatory field 311 near the clip. At the same time, the positioning element 308 engages with said positioning body 309 of the console 302 firmly to position the holder 306 in a desired location near to where the surgeon stands or seats during surgery. The positioning body 309 may also be concave, or may comprise a slot, or may have a positioning surface suitably treated or machined in order to engage with the positioning element 308. The positioning element 308 may have any shape and feature to engage with said positioning surface. For example, the positioning element 308 may comprise a snap-fit device, or the positioning element 308 may comprise attachment means for engaging with said positioning body. According to an embodiment, the positioning element 308 comprises a clip mechanically and detachably engaging the positioning body 309. According to an embodiment, the clip of the positioning element 308 snap fits to the positioning body 309 of the console 302, and preferably in this embodiment the positioning body 309 comprises said convex body. Said positioning element 308 is suitable for position the cavity 345 of the sterile holder 306 at a desired location near the console 302 and within the sterile operatory field 311.

The provision of said cavity 345 of said at least one sterile holder 306 allows the surgeon to drop the at least one mechanically ungrounded master input handle 310 within the cavity 345 and to make it rest on said at least one resting element 307 of the at least one sterile holder 306. Thanks to said cavity 345 of the at least one sterile holder 306, the at least one mechanically ungrounded master input handle 310 results boxed in the sterile holder 306 within the sterile operatory field 311 when is not hand held by the surgeon. According to an embodiment, said at least one sterile holder 306 has a box-like body provided with an opening 333 to access the cavity 345, preferably facing the surgeon and/or facing upwards when in operative conditions.

The positioning element 308 may be located on the outer surface 332 of the at least one sterile holder 306, and its particular location may be chosen with the purpose to position the at least one sterile holder 306 for receiving the at least one mechanically ungrounded master input handle 310 in a desired location within the sterile operatory field 311.

Figure 6B:
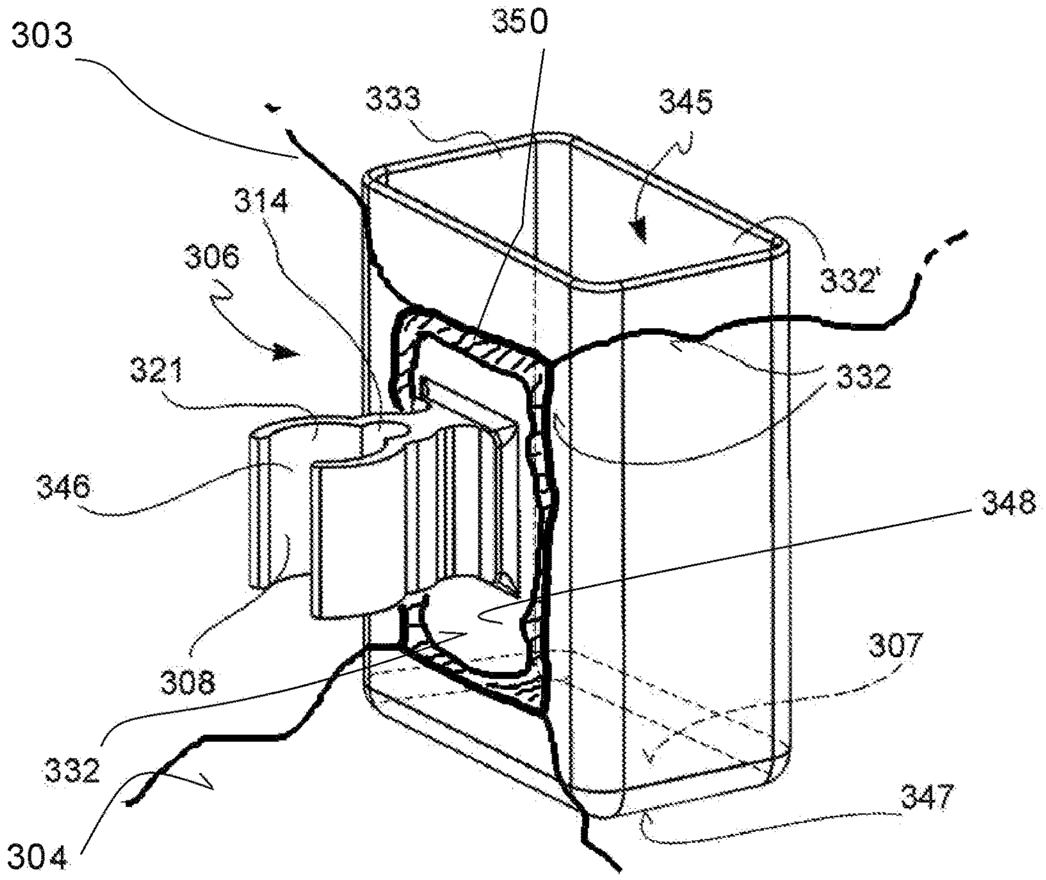

According to a preferred embodiment, the at least one sterile holder 306 is integral with the sterile drape 303, as shown for example in FIG. 6B. For example, the sterile holder 306 is welded or glued to the outer surface of the sterile drape. The positioning element 308 may be integral with the sterile drape 303 and at the same time detachably engaged with the positioning body 309. The sterile drape 303 may be attached to the at least one sterile holder 306, and preferably to the outer surface 332 thereof, and may comprise a through passage 348 for allowing the positioning element 308, for example comprising a clip, to pass there through, while preserving the integrity of the sterile barrier. According to an embodiment, the positioning element 308 is integral with the outer surface 332 of the sterile holder 306, although they may be made in separate pieces, so that to rigidly determine the position and spatial orientation of the resting element 307, for example a resting surface 307, relative to the positioning body 309 of the console 302 where the positioning element 308, for example comprising a clip, is engaged. According to a preferred embodiment, said clip of the positioning element 308 acts as constraining element for locally constraining the surgical drape 303 against said positioning body 309 of the master sterile console 302, in order to locally reduce the volumetric encumber of the surgical drape 303. The surgical drape 303 may have a loose body that drapes air other than the console 302, therefore thanks to the provision of said positioning element 308 comprising said clip is allowed to constrain a portion of the drape 303 to a portion of the console 302, preferably at or near the at least one positioning body 309 of the console 302. Thereby, the at least one clip at the same time locally close-fits the body of the sterile drape 303 against the positioning body 309 of the console 302 and holds the at least one sterile holder 306 in place within the sterile operatory field 311.

According to an embodiment, said clip of the positioning element 308 comprises at least one cable guide 314 for guiding a cabled connection 315 for example of the console 302. Thereby, the clip has the further advantage of guiding the cabled connection 315, for example a power supply and/or a data cable of said master console 302. For example, said cable guide 314 comprise a groove for receiving an elongated body dig in a wall of the clip facing the outer surface 305 of the body of the surgical drape 303. Preferably, said clip of the positioning element 308 has an arched concave surface 321 facing said outer surface 305 of the surgical drape 303 so to be suitable for fitting said convex body of the positioning body 309 of the console 302. For example, the arched concave surface 321 of said at least one clip 308 describes substantially the profile of a “C”.

Figure 4:
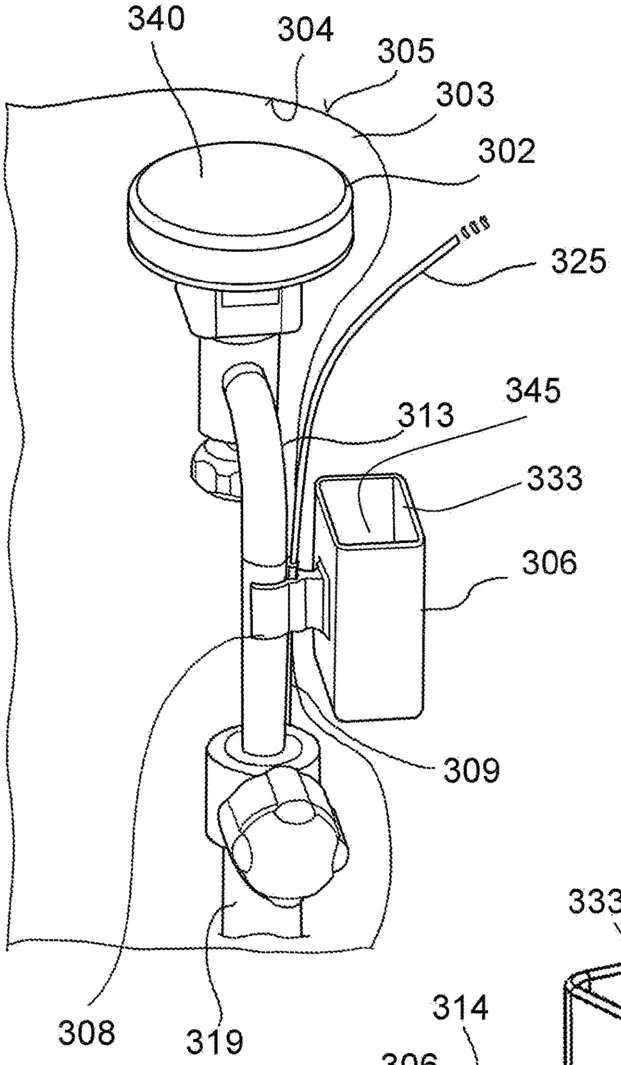
FIG. 4 is an axonometric view that shows a portion of a console covered by a surgical drape and a sterile holder, according to an embodiment.
Figure 5:
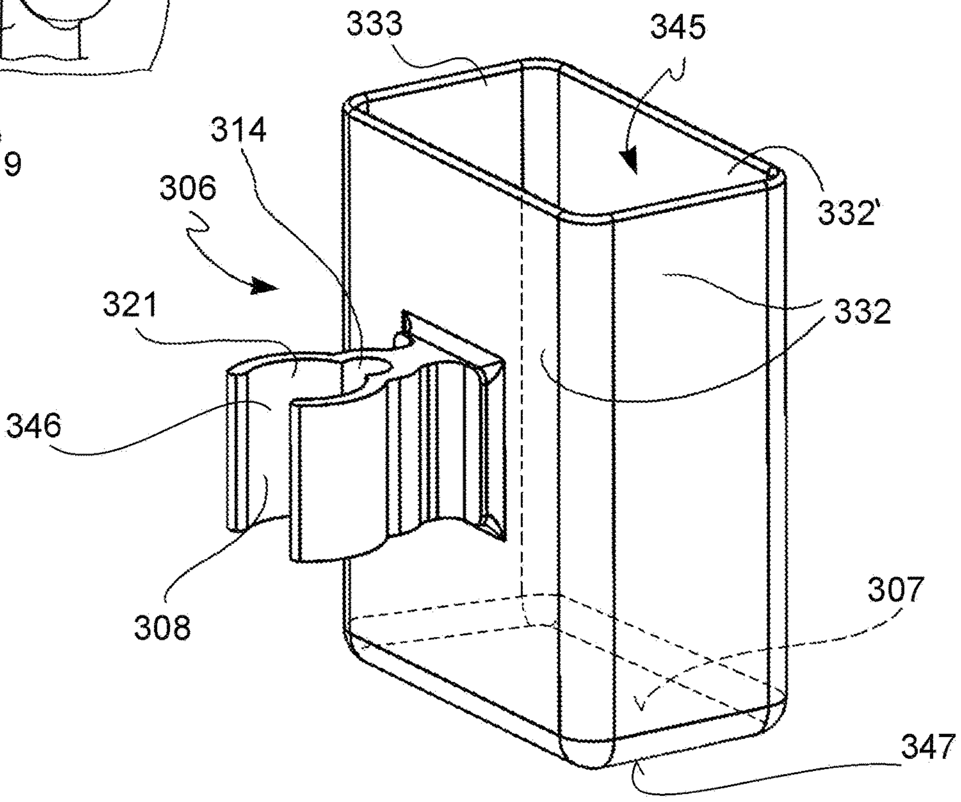
FIG. 5 is an axonometric view that shows a sterile holder, according to an embodiment.

According to a preferred embodiment as shown for example in FIG. 4, said at least one resting element 307 comprises a resting surface 307, for example said resting surface 307 is a surface of a bottom wall 347 of said sterile holder 306 facing the cavity 345.

According to an embodiment, said resting surface 307 for supporting at least a portion of an ungrounded master input handle 310 to rest thereon is a bottom surface of a basket, i.e. a substantially cup-shaped container, and said basket corresponds to the sterile holder 306. According to an embodiment, said holder 306 is designed for temporary supporting a master input tool 310 when not hand-held by a surgeon within the sterile operatory field 311, and the at least one resting surface 307 comprises a bottom surface of the at least one sterile holder 306.

As previously mentioned, said at least one sterile holder 306 comprises an opening 333 for the access to said cavity 345. Preferably, said opening 333 is opposite to said resting surface 307 in respect of said cavity 345. According to an embodiment, the at least one sterile holder 306 also comprises side surfaces 332 delimiting the opening 333 and the cavity 345. Thereby, the surgeon is allowed to drop the at least one ungrounded master input tool 310 on a sterile resting surface 307 exposed within a sterile operatory field 311, during surgery. Thanks to the provision of such a surface 307, a surgeon may alternate hand microsurgery and robotic-aided microsurgery during a single intervention, without for this reason compromise the sterility of the sterile operatory field 311. Thereby, it is avoided the need of sterilize the ungrounded master input tool 310 each time the surgeon switches from hand microsurgery to robotic-aided microsurgery and vice-versa during a single surgical intervention.

Said side surfaces 332' face towards the cavity 345 and said outer surfaces 332 face opposite, and preferably said positioning element 308 is integrally connected to at least one of said outer surfaces 332. According to an embodiment, said outer surface 332 is substantially flat to favor the attachment of the clip of the positioning element 308. The orientation of the clip, i.e. the direction of longitudinal extension of the “C” shaped seat 346 defined by said arched surface 321 of said clip of the at least one sterile holder 306, may be substantially aligned with the direction of development of the cavity 345 of the at least one sterile holder 306. Thereby, the cavity 345 may be delimited by said resting surface 307, said bottom wall 347, said side surfaces 332'.

According to a variation, said clip of the positioning element 308 and the side surface 332' of the at least one sterile holder 306 defining said cavity 345 may have a relative degree of freedom for adjusting the position of the cavity 345 upon engagement of the clip with the positioning body 309, for example a hinge or a rotative joint such as a universal joint, may be provided articulating the clip 308 and the side surface 332' of the sterile holder 306 for rotating the holder 306 when the clip 308 is engaged with said positioning body 309 of the console 302 and/or a slider connects the clip and the outer surface 332 of said at least one sterile holder 306.

According to a preferred embodiment, said positioning body 309 of the console 302 faces towards the inner surface 304 of the surgical drape 303. Thereby, it is avoided the need of sterilizing the positioning body 309 of the console 302. According to an embodiment, said at least one positioning body 309 comprises at least one convex surface 313, so that said clip of the positioning element 308 engages said convex surface 313. According to an embodiment, the sterile drape 303 is interposed between the positioning body 309 of the console 302 and the at least one sterile holder 306. According to an embodiment, the body of the sterile drape 303 is interposed between, preferably in contact with both, the clip of the positioning element 308 and the positioning body 309 of the console 302. According to an embodiment, the body of the sterile drape 303 is interposed between, preferably in contact with both, said arched surface 314 of the clip and said convex surface 313 of the positioning body 309 of the console 302.

Figure 1:
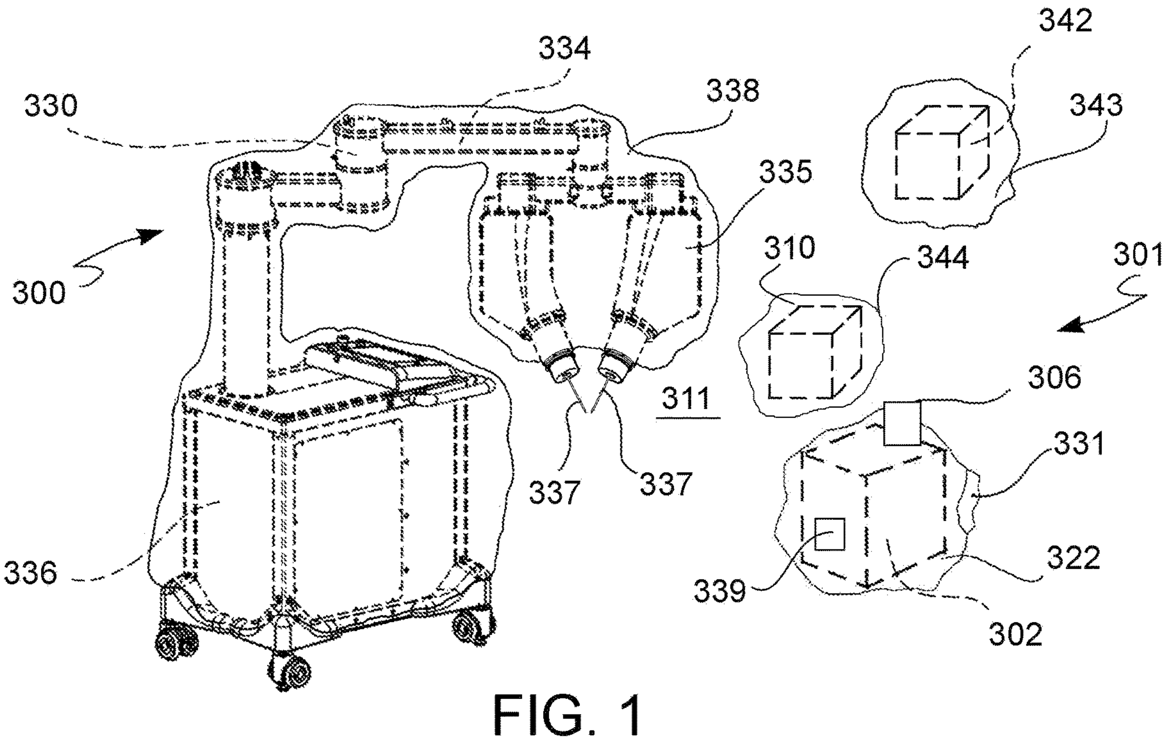
FIG. 1 is an axonometric view that diagrammatically shows a surgical robotic system located within a sterile operatory field and having a master workstation, according to an embodiment.
Figure 2:
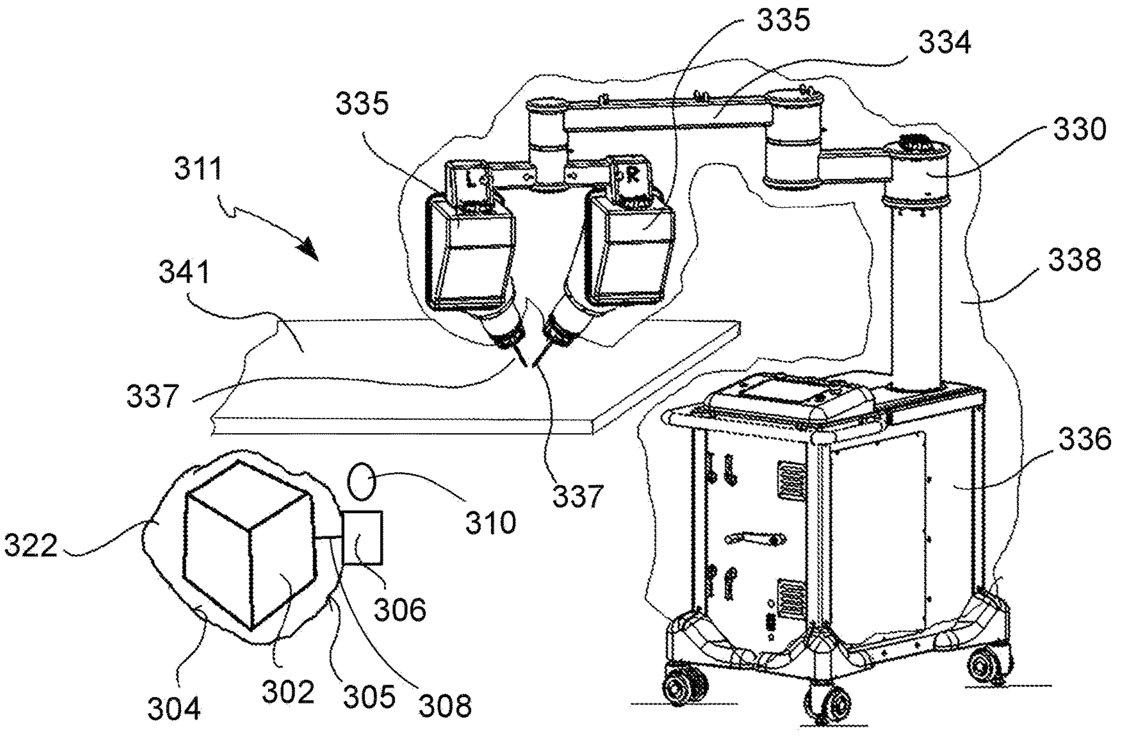
FIG. 2 is an axonometric view that diagrammatically shows a surgical robotic system located within a sterile operatory field near an operatory bed, according to an embodiment.
Figure 3:
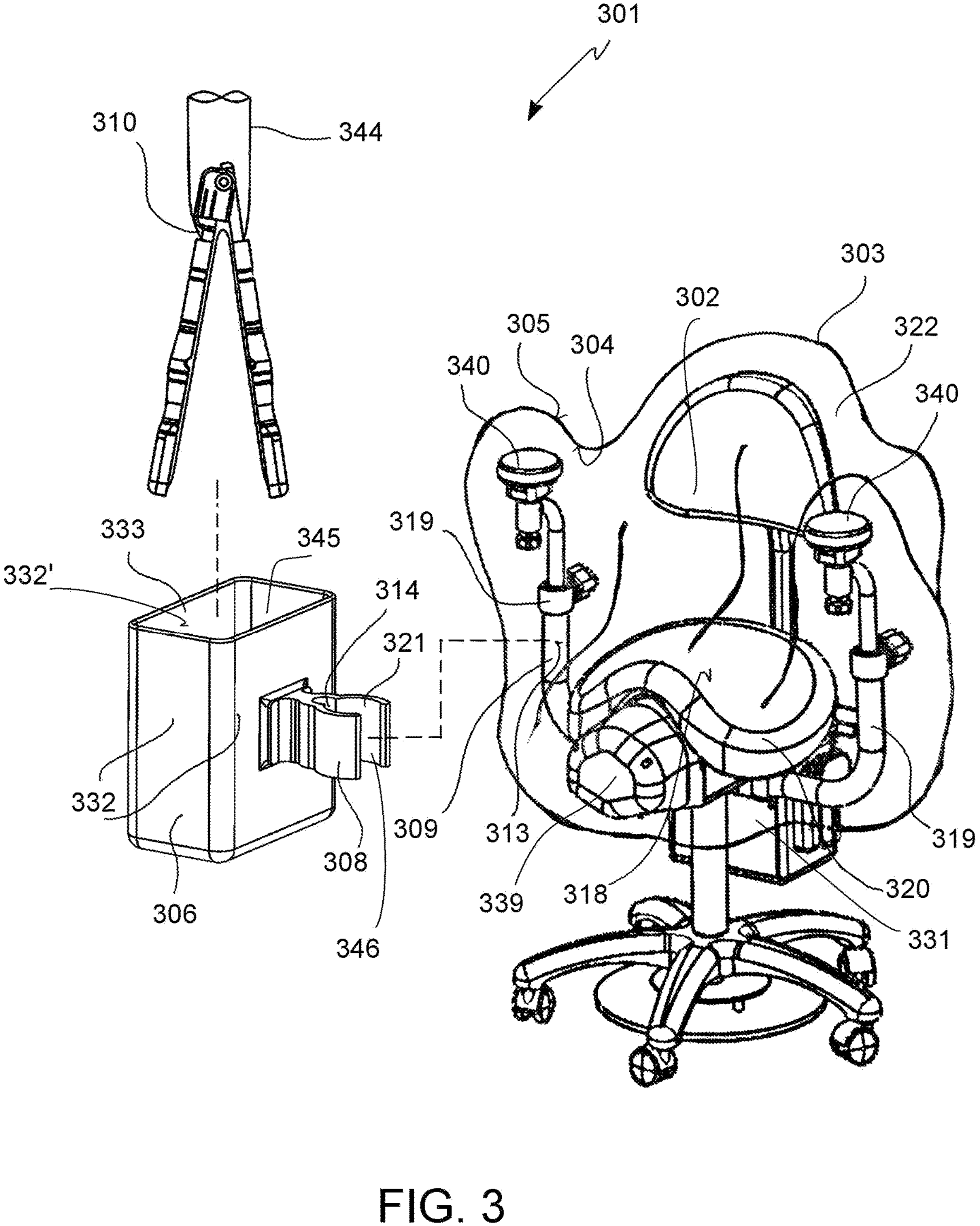
FIG. 3 shows diagrammatically in axonometric view a master workstation comprising a surgical chair, a sterile holder and a draped master input handle, according to an embodiment.

According to an embodiment as shown for example in FIG. 3, said console 302 comprises a surgical chair 320. The word "chair" used herein is intended to also encompass a "saddle stool". According to a preferred embodiment, said at least one positioning body 309 is a an upright 319 of a surgical chair 320 of a the console 302. According to a preferred embodiment, said at least one positioning body 309 is an upright 319 of a surgical chair 320 supporting an armrest 340, preferably of rounded shape so that the surgeon can rest the elbow thereon. According to an embodiment, said chair 320 comprises at least one armrest 340 having said positioning body 309, for example a connecting element connecting the armrest to a seating surface 318 of said chair 320, and said positioning element 308 of the sterile holder 306 engages said positioning body 309 of the armrest 340.

According to an embodiment, said console 302, for example said chair 320, is provided with a tracking field generator 339 designed to track the position and orientation of the at least one mechanically ungrounded master input handle 310.

The tracking field generator 339 may be an optical tracking field generator such as at least one camera of a stereoscopic camera set.

As previously described, a master workstation 301 for a surgical robotic system 300 suitable for being located within a sterile operatory field 311 comprise at least one ungrounded master input handle 310, suitable for being hand-held by a surgeon during surgery for controlling a slave robotic assembly 330 of said surgical robotic system 300, and a console 302, and a sterile drape 303 draping at least a portion of said console 302 forming at least partially a sterile barrier, and at least one sterile holder 306, wherein said at least one sterile holder 306 comprises at least one cavity 345 and at least one opening 333 to access said at least one cavity 345, and at least one resting element 307 within said cavity 345 suitable for the master input handle 310 to rest thereon when said master input handle 310 is not hand-held.

According to an embodiment, said at least one sterile holder 306 is associated to the outer surface 305 of the surgical drape 303.

According to an embodiment, said at least one sterile holder 306 is glued to the outer surface 305 of the surgical drape 303. Said outer surface 305 of the surgical drape 303 may comprise an adhesive layer, such as an adhesive strip to attach the at least one sterile holder 306 to the outer surface 305 of the sterile drape 303. In such a case, the at least one sterile holder 306 may comprise a mark and/or a sign, acting as positioning element 308.

According to an embodiment, said at least one sterile holder 306 is detachably associated to the outer surface 305 of the surgical drape 303.

According to an embodiment, said at least one sterile holder 306 comprises at least one positioning element 308 to position the at least one sterile holder 306 at a desired location near the console 302 and within the sterile operatory field 311.

According to an embodiment, said at least one positioning element 308 of the at least one sterile holder 306 is engaged with at least one positioning body 309 of the console 302 through said sterile drape 303 while preserving the integrity of the sterile barrier. According to an embodiment, said positioning element 308 rigidly determines the relative position and spatial orientation of said resting surface 307 within said cavity 345 and said convex body 309 of the console 302.

According to an embodiment, said positioning element 308 is detachably engaged with said positioning body 309 of the console 302.

According to an embodiment, said positioning element 308 comprises a positioning clip elastically engaging a positioning body 309 of the console 302. The clip is preferably elastically loaded. According to an embodiment, said positioning element 308 comprises at least one flap 312 to detach the positioning element 308 from the positioning body 309 of the console 302. The flap 312 may be elastically loaded and cooperating with the clip of the positioning element 308. Said positioning element 308 may comprise a pair of flaps 312. The flap 312 may act as a handle for releasing the clip of the positioning element 308. The clip may be formed by two pieces elastically connected, and the at least one flap 312 is attached to one of said two pieces of the clip. Two flaps 312 may be provided, each flap 312 being attached to one of said two pieces of the clip. The provision of said at least one flap 312 may determine to open the clip of the positioning element thereby avoiding scratching the surgical drape 303 during detachment of the clip. Thereby the clip may have a stronger elastic clamping force without compromising the integrity of the sterile drape 303.

According to an embodiment, said positioning body 309 of the console 302 comprises a convex body.

According to an embodiment, said positioning element 308 acts as constraining element for locally constraining the surgical drape 303 against said positioning body 309 of the master sterile console 302.

According to an embodiment, said ungrounded master input handle 310 include a cabled connection 325 and positioning element 308 acts as constraining element for locally constraining said cabled connection 325 against said positioning body 309 of the master sterile console 302.

According to an embodiment, said at least one positioning element 308 of the at least one sterile holder 308 comprises an adhesive layer. Preferably, the outer surface 332 of the at least one sterile holder 306 comprises said adhesive layer.

According to an embodiment, said at least one sterile holder 306 is in single piece with the surgical drape 303.

According to an embodiment, said opening 333 of the at least one sterile holder 306 opens on the outer surface 305 of the surgical drape 303.

According to an embodiment, the master workstation 301 comprises a further sterile holder 306 so that to comprise at least two sterile holders 306, and a further ungrounded master input handle 310, so as to comprise two master input handles 310, wherein preferably each sterile holder 306 is for individually housing one master input handle 310. According to an embodiment, said two sterile holders 306 are spaced apart on the same outer surface 305 of the same surgical drape 303.

According to an embodiment, said two sterile holders 306 are attached to different positioning bodies 309 of the console 302. For example, said different positioning bodies 309 of the console 302 are spaced apart.

According to an embodiment, said two sterile holders 306 are attached to a same positioning body 309 of the console 302.

According to an embodiment, said console 302 comprises a chair 320 and wherein said surgical drape 303 covers said chair 320.

According to an embodiment, said console 302 comprises a tower 315 and wherein said surgical drape 303 covers said tower 315, as diagrammatically shown in FIG. 12. The tower may comprise a screen 316. The screen 316 may display a portion of the sterile operatory field 311 such as a portion of the slave workspace where the at least one surgical instrument 337 operates. The tower 315 may comprise ground contact units, such as a plurality of wheels. An optical and/or magnetic tracking field generator 339 may be provided integral with said tower 315 to track position and orientation of the at least one ungrounded master input handle 310. The tower 315 of the console 302 may be equipped by said positioning body 309, for example a convex body.

According to a general embodiment, it is provided a sterile operatory field 311 comprising at least one master workstation 301 according to any one of the embodiments above.

The sterile operatory field 311 comprises at least one operatory bed 341 providing a support for a patient's anatomy to be treated.

According to an embodiment, the sterile operatory field 311 is delimited by a sterile barrier formed by at least one sterile drape 303. According to an embodiment, the sterile barrier is formed by at least one sterile drape 303 and by at least a portion of the at least one sterile holder 306, and preferably by at least a portion of the outer wall 332 of the at least one sterile holder 306. The positioning element 308 of the at least one sterile holder 306 may be located within the sterile operatory field 311 or may be located out of the sterile operatory field 311.

Thanks to such a master workstation 301, the integrity of the sterile operatory 311 field is preserved, as well as the sterility of the operatory field 311.

According to an embodiment, said sterile operatory field 311 further comprises a slave robotic assembly 330 controlled by said master workstation 310.

According to a general embodiment, it is provided a surgical robotic system 300 comprising at least one master workstation 301 according to any one of the embodiments above.

According to a preferred embodiment, said system 300 further comprises a slave robot assembly 330 comprising at least one surgical arm 334 suitable for manipulating at least one surgical instrument 337, and preferably said at least one surgical arm comprises at least one motorized manipulator 335 controlled by said master workstation 301 manipulating said at least one surgical instrument 337.

According to an embodiment, said slave robot assembly 330 comprises at least one surgical arm 334 manipulating said surgical instrument 337. According to an embodiment, said salve robot assembly 330 comprises at least one micromanipulator 335 manipulating said surgical instrument 304. Preferably, said at least one micromanipulator 335 is directly connected in series to said surgical arm 334 forming a kinematic chain with said surgical arm 334 and manipulates said surgical instrument 337. According to an embodiment, at least two micromanipulators 335 are directly connected in series to said surgical arm 334 forming an at least two-branched kinematic chain with said surgical arm 334. According to an embodiment, said slave robot assembly 330 comprises at least one robotic cart 336 and said at least one arm 334 extends from the robotic cart 336.

Preferably, said robotic surgery system 300 comprises a control unit, suitable for receiving at least a position and orientation associated to said at least one mechanically ungrounded master input handle 310 and suitable for transmitting a command signal to the slave robot assembly 330 in order to actuate said surgical instrument 337.

According to a preferred embodiment, said control unit is suitable for receiving a first command signal containing information about said manual command and to transmit a second command signal containing information about said manual command to the slave robot assembly 330 in order to actuate said surgical instrument 337. According to a preferred embodiment, said robotic microsurgery system 300, and preferably said draped console 302 of said robotic microsurgery system 300, further comprises at least one tracking system comprising a field generator 339, suitable to detect within a predefined tracking volume position and orientation of said master input tool 310, For example, said field generator 339 is a magnetic and/or optical field generator is located integral with the seating surface 318 of the chair 320 of the console 302. At least one slave drape 338 may be provided to drape at least a portion of the robotic slave assembly 330.

According to a preferred embodiment, said robotic microsurgery system 300 further comprises at least one surgical microscope 342. A microscope drape 343 may be provided for draping at least a portion of the microscope 342.

According to an embodiment, said sterile operatory field 311 further comprises at least a portion of at least one robotic slave manipulator 330 according to any one of the embodiments described above. Thereby, said sterile operatory field 311 further comprises at least a portion of at least one robotic surgery system 300 according to any one of the embodiments described above.

According to an embodiment, said sterile operatory field 311 comprises said robotic surgery system 300.

Thereby, it is allowed the surgeon to alternate hand microsurgery and robotic-aided microsurgery during a single intervention, without for this reason needing to sterilize the master console.

Thanks to the provision of such at least one sterile holder 306, it is provided a solution able to drape master console 302 preserving sterility and at the same time making the at least one ungrounded master input handle 310 easier to manipulate within a sterile operatory field 311, even when the surgeon switches to hand microsurgery, enabling the surgeon to switch back to the robot-aided microsurgery as desired while allowing the surgeon to drop or grasp the mechanically ungrounded master input handle 310 with minimum efforts, as the cavity 345 of the at least one sterile holder 306 is located in a desired location near within the sterile operatory field 311.

According to an embodiment, the cavity 345 of the at least one sterile holder 306 has a depth that is shallower than the length of the ungrounded master input handle 310 so that a portion of the ungrounded master input handle 310 pops out of the opening 333, making simpler for the surgeon to grasp the mechanically ungrounded master input handle 310 from the resting element 307 within the cavity 345 of the sterile holder 306.

In the following a method for performing surgery will be described.

A method for performing surgery, and preferably robotic-aided surgery, comprises the following steps.

The method comprises the step of providing a master workstation 301 within a sterile operatory field 311, wherein preferably the master workstation 301 comprises at least one mechanically ungrounded master input handle 310 suitable for being held in hand of the surgeon to control a slave robotic assembly comprising at least a surgical instrument 337. The master workstation 310, the sterile operatory field 311 and the slave robotic assembly 330 may be any as described in any of the embodiments above.

The positioning element 308 may mechanically engage the positioning body 309 of the console 302.

The method comprises the step of draping a console 302 of the master workstation 301, preferably by means of a surgical drape 303.

According to a mode of operation, the method comprises the step of associating at least one sterile holder 306 to the outer surface 305 of the surgical drape 303. That may open at least one opening 333 for accessing a cavity 345 on the outer surface 305 of the surgical drape 303.

According to a mode of operation, the method comprises the step of associating at least one sterile holder 306 to the outer surface 305 of the surgical drape 303 in a detachable manner. According to a mode of operation, the method comprises the step of detaching the at least one sterile holder 306 from the outer surface 305 of the surgical drape 303.

According to a mode of operation, the method comprises the step of associating at least one sterile holder 306 to the outer surface 305 of the surgical drape 303 in a detachable manner by means of mechanically engaging said positioning element 308, for example said clip, of at least one sterile holder 306 with a positioning body 309 of the console 302, the positioning body 309 being preferably a convex body. This step may comprise acting on said at least one flap 312 of the at least one sterile holder 306. Acting on said at least one flap 312 may determine the positioning element 308, such as said clip, to open. According to a mode of operation, the method comprises the step of detaching at least one sterile holder 306 from the outer surface 305 of the surgical drape 303 by means of mechanically disengaging said positioning element 308, for example said clip, from said at positioning body 309 of the console 302, the positioning body 309 being preferably a convex body.

According to a mode of operation, the method comprises the step of clipping a sterile holder 306 to a positioning body 309 of the console 302 so that a holder cavity 345 is within the sterile operatory field 311. The step of clipping may comprise said step of acting on said at least one flap 312.

According to a mode of operation, the method comprises the step of defining a desired location within the sterile operatory field 311 with the aim of positioning the sterile holder 306 there.

According to a mode of operation, the method comprises the step of holding in hand the mechanically ungrounded master input handle 310, with the purpose of controlling said surgical instrument 337 of the slave robotic assembly 330.

The method comprises the further step of dropping or resting at least one ungrounded master input handle 310 within said cavity 345 of the at least one sterile holder 306 so that the ungrounded master input handle 310 rests on a resting element 307 within the cavity 345.

According to a mode of operation, the method comprises the further step of lifting or grasping the at least one ungrounded master input handle 310 from the sterile holder 306, and preferably from the resting element 307 within the cavity 345 of the sterile holder 306 placed in a desired location within the sterile operatory field 311, thereby holding again in hand the master input handle 310.

Preferably the method is carried out by a master workstation 301 and/or a sterile operatory field 311 and/or a surgical robotic system 300 according to any of the embodiments described above.

Thanks to the features described above, provided either disjointly or together in particular embodiments, it is possible to respond to the above-mentioned needs providing the above cited advantages, and in particular:

- the surgeon is able to easily drop the ungrounded master controller within the cavity of the sterile holder at any time during surgery;
- the sterility of the operatory field is maintained;
- the volumetric encumber of the sterile drape covering the console may be reduced;
- it is reduced the risk of braking the sterile drape;
- it is maintained the integrity of the sterile barrier that surrounds the sterile operatory field;
- the holder may acts as a sterile holster within the sterile operatory field for receiving the ungrounded master input tool when is not hand-held, for example during alternation of hand surgery and robotic microsurgery;
- the sterile drape may be held in place by a sterile holder having a positioning clip.

To the embodiments described above, one skilled in the art may, to satisfy contingent and specific needs, make numerous modifications, adaptations and replacements of elements with others that are functionally equivalent, without however departing from the scope of the appended claims.

LIST OF REFERENCES

300 Surgical robotic system
301 Master workstation
302 Console
303 Surgical drape or sterile drape
304 Inner non-sterile surface of the drape
305 Outer sterile surface of the drape
306 Sterile holder, or holder
307 Resting element, or resting surface
308 Positioning element
309 Positioning body of the console
310 Mechanically ungrounded master input handle or master input tool
311 Sterile operatory field
312 Flap of the positioning element
313 Convex surface of the convex body
314 Cable guide
315 Tower of the console
316 Screen
318 Seating surface, or saddle seating surface
319 Connecting element of the armrest
320 Surgical chair, or saddle stool, of the console
321 Arched clip surface
322 Drape cavity
325 Cabled connection
330 Slave robotic assembly
331 Opening of the drape

332 Outer surface of the holder
332' Side surface of the holder
333 Opening of the holder
334 Robotic arm
335 Motorized manipulators
336 Robotic cart
337 Surgical instrument
338 Slave drape
339 Tracking field generator
340 Armrest
341 Operatory bed
342 Surgical microscope
343 Microscope drape
344 Master drape
345 Cavity of the holder
346 Seat of the clip
347 Bottom wall of the holder
348 Through passage or through hole of the drape
350 Boundary of the though passage

The invention claimed is:

1. A master workstation for a surgical robotic system suitable for being located within a sterile operatory field, the master workstation comprising:

at least one ungrounded master input handle suitable for being hand-held by a surgeon during surgery for controlling a slave robotic assembly of said surgical robotic system;

a console;

a sterile drape draping at least a portion of said console forming at least partially a sterile barrier, said sterile drape comprising an inner surface facing the console and an outer surface facing the sterile operatory field; and at least one sterile holder, wherein said at least one sterile holder comprises:

at least one cavity and at least one opening to access said at least one cavity; and at least one resting element within said cavity and suitable for the master input handle to rest thereon when said master input handle is not hand-held wherein said at least one sterile holder is attached to the outer surface of the sterile drape and said at least one sterile holder is made of loose plastic material.

2. The master workstation according to claim 1, wherein said at least one sterile holder is glued to the outer surface of the sterile drape.

3. The master workstation according to claim 1, wherein said at least one sterile holder is detachably attached to the outer surface of the sterile drape.

4. The master workstation according to claim 1, wherein said at least one sterile holder comprises at least one positioning element to position the at least one sterile holder at a desired location near the console and within the sterile operatory field.

5. The master workstation according to claim 4, wherein said at least one positioning element of the at least one sterile holder is engaged with at least one positioning body of the console through said sterile drape while preserving the integrity of the sterile barrier.

6. The master workstation according to claim 4, wherein said at least one positioning element of the at least one sterile holder comprises an adhesive layer.

7. The master workstation according to claim 1, wherein said at least one sterile holder is in single piece with the sterile drape.

8. The master workstation according to claim 1, wherein said opening of the at least one sterile holder opens on the outer surface of the sterile drape.

9. The master workstation according to claim 1, comprising a further sterile holder so that so as to comprise at least two sterile holders, and a further ungrounded master input handle, so as to comprise two master input handles, wherein each sterile holder is for individually housing one master input handle.

10. The master workstation according to claim 9, wherein said two sterile holders are spaced apart on the same outer surface of the same sterile drape.

11. The master workstation according to claim 1, wherein said console comprises a chair and wherein said sterile drape covers said chair.

12. The master workstation according to claim 1, wherein said console comprises a tower and wherein said sterile drape covers said tower.

13. A robotic surgery system comprising at least one master workstation according to claim 1 and a slave robotic assembly controlled by said master workstation.

14. A sterile operatory field comprising:

at least one master workstation according to claim 1; and at least one operatory bed providing a support for a patient's anatomy to be treated.

15. The master workstation according to claim 1, wherein said at least one sterile holder is made of flexible plastic material.

16. The master workstation according to claim 5, wherein said at least one positioning body of the console comprises a convex body, and wherein said at least one positioning element rigidly determines a relative position and spatial orientation of said resting surface within said cavity and said convex body of the console.

17. The master workstation according to claim 5, wherein said at least one positioning element is detachably engaged with said at least one positioning body of the console, and wherein said at least one positioning element acts as constraining element for locally constraining the sterile drape against said at least one positioning body of the master sterile console.

18. The master workstation according to claim 5, wherein said at least one positioning element comprises a positioning clip elastically engaging a positioning body of the console.

19. The master workstation according to claim 18, wherein said at least one positioning element comprises at least one flap to detach the at least one positioning element from the at least one positioning body of the console.

20. The master workstation according to claim 5, wherein said ungrounded master input handle includes a cabled connection and the at least one positioning element acts as a constraining element for locally constraining said cabled connection against said at least one positioning body of the master sterile console.

* * * * *